(12) United States Patent
Golden

(10) Patent No.: US 9,066,889 B2
(45) Date of Patent: Jun. 30, 2015

(54) NON-FLUORIDE CONTAINING DIETARY SUPPLEMENT TOOTHPASTE AND METHODS OF USING THE SAME

(75) Inventor: Bruce Alan Golden, Hewlett Harbor, NY (US)

(73) Assignee: GOLDEN PRODUCTS LLC, Howard Beach, NY (US)

( * ) Notice: Subject to any disclaimer, the term of this patent is extended or adjusted under 35 U.S.C. 154(b) by 776 days.

(21) Appl. No.: 12/454,674

(22) Filed: May 21, 2009

(65) Prior Publication Data
US 2010/0297197 A1 Nov. 25, 2010

(51) Int. Cl.
| | | |
|---|---|---|
| A61Q 11/00 | (2006.01) | |
| A61K 8/84 | (2006.01) | |
| A61K 8/19 | (2006.01) | |
| A61K 8/23 | (2006.01) | |
| A61K 8/27 | (2006.01) | |
| A61K 8/365 | (2006.01) | |
| A61K 8/42 | (2006.01) | |
| A61K 8/55 | (2006.01) | |
| A61K 8/67 | (2006.01) | |
| A61K 8/96 | (2006.01) | |
| A61K 8/25 | (2006.01) | |
| A61K 8/29 | (2006.01) | |
| A61K 8/34 | (2006.01) | |
| A61K 8/368 | (2006.01) | |
| A61K 8/46 | (2006.01) | |

(52) U.S. Cl.
CPC ... *A61K 8/84* (2013.01); *A61K 8/19* (2013.01); *A61K 8/23* (2013.01); *A61K 8/27* (2013.01); *A61K 8/365* (2013.01); *A61K 8/42* (2013.01); *A61K 8/55* (2013.01); *A61K 8/67* (2013.01); *A61K 8/671* (2013.01); *A61K 8/673* (2013.01); *A61K 8/675* (2013.01); *A61K 8/678* (2013.01); *A61K 8/965* (2013.01); *A61Q 11/00* (2013.01); *A61K 8/25* (2013.01); *A61K 8/29* (2013.01); *A61K 8/345* (2013.01); *A61K 8/368* (2013.01); *A61K 8/463* (2013.01)

(58) Field of Classification Search
CPC . A61K 2300/00; A61K 8/11; A61K 2800/48; A61K 8/671; A61Q 11/00
USPC ........................................... 424/49, 401
See application file for complete search history.

(56) References Cited

U.S. PATENT DOCUMENTS

| | | | | |
|---|---|---|---|---|
| 3,929,987 | A | * | 12/1975 | Colodney et al. ............... 424/52 |
| 3,943,240 | A | | 3/1976 | Delaney et al. |
| 3,991,177 | A | * | 11/1976 | Vidra et al. ..................... 424/50 |
| 4,123,517 | A | | 10/1978 | Baines et al. |
| 5,531,982 | A | * | 7/1996 | Gaffar et al. .................... 424/49 |
| 5,624,906 | A | * | 4/1997 | Vermeer ......................... 514/23 |
| 2001/0044475 | A1 | * | 11/2001 | Matsuzaki et al. ............. 516/100 |
| 2003/0152524 | A1 | * | 8/2003 | Eshita ............................. 424/49 |
| 2003/0170185 | A1 | * | 9/2003 | Takatsuka et al. ............. 424/52 |
| 2005/0152851 | A1 | * | 7/2005 | Kaminski ....................... 424/49 |
| 2006/0057213 | A1 | * | 3/2006 | Larhrib et al. ................ 424/489 |
| 2006/0142351 | A1 | * | 6/2006 | Murray ......................... 514/356 |

FOREIGN PATENT DOCUMENTS

| | | | | |
|---|---|---|---|---|
| KR | 2005058069 | A | * | 6/2005 |
| KR | 10-0564231 | B1 | | 3/2006 |

OTHER PUBLICATIONS

Drugs.com, Pantothenic Acid (Systemic), http://web.archive.org/web/20080726171547/http://www.drugs.com/mmx/calcium-pantothenate.html, pp. 1-8, Jul. 2008.*
CTFA International Cosmetic Ingredient Dictionary, 4th edition, published by The Cosmetic, Toiletry, and Fragrance Association Washington D.C.
U.S. Patent and Trademark Office Final Office Action dated Nov. 7, 2014 in U.S. Appl. No. 12/454,674.

* cited by examiner

*Primary Examiner* — Frederick Krass
*Assistant Examiner* — Tracy Liu
(74) *Attorney, Agent, or Firm* — Dilworth & Barrese, LLP

(57) ABSTRACT

A non-fluoride containing toothpaste enriched with at least one dietary supplement. The non-fluoride containing toothpaste comprising a dentally acceptable oral vehicle containing a sufficient amount of thickening agent to impart a pasty consistency; and at least one dietary supplement wherein a serving size portion of the non-fluoride containing toothpaste contains more than about 2 percent of the reference daily intake (RDI) of the dietary supplement.

20 Claims, No Drawings

NON-FLUORIDE CONTAINING DIETARY SUPPLEMENT TOOTHPASTE AND METHODS OF USING THE SAME

TECHNICAL FIELD

The present disclosure generally relates to oral hygiene products, and more particularly to oral hygiene products containing dietary supplements, and methods of use thereof.

BACKGROUND

Oral hygiene products, such as toothpastes, have been in use for many years. Toothpastes generally include an abrasive material which is dispersed in a gel or paste base. Abrasives remove stains and plaque, as well as polish teeth. Common abrasives include calcium phosphates, alumina, calcium carbonate, and silica. Toothpaste must be abrasive enough to remove plaque and stains, but should not be so abrasive as to damage tooth enamel.

Fluoride is typically added to toothpaste in order to reduce tooth decay. In particular, fluoride incorporates itself into tooth enamel to make teeth more resistant to acids produced by plaque bacteria, as well as acids found in fruit juices, soda and certain foods. Indeed, toothpastes containing fluoride hardens tooth enamel to make the entire tooth structure more resistant to decay and promote remineralization, which aids in repairing early decay. In toothpaste, fluoride is commonly found in the form of sodium monofluorophosphate, stannous fluoride, or sodium fluoride. Notably, due to the toxicity of fluoride, the Food and Drug Administration (FDA) regards any toothpaste containing fluoride as a drug. Accordingly, the FDA requires a warning on the label of any toothpaste containing fluoride stating "If you accidentally swallow more than used for brushing, seek professional help or contact a poison control center immediately." Moreover, the American Dental Association (ADA) requires that toothpaste manufacturers include the following language on all ADA-Accepted toothpastes containing fluoride: "Do not swallow. Use only a pea-sized amount for children under six. To prevent swallowing, children under six years of age should be supervised in the use of toothpaste." Clearly, toothpastes containing fluoride are not intended to, and should not, be swallowed.

Detergents may also be added to toothpastes to aid in cleaning. For example, detergents may be added to create a foaming action. Foam prevents toothpaste from dribbling out one's mouth during brushing. SLS (sodium lauryl sulfate) is a commonly used detergent.

Toothpastes may also include other ingredients such as, for example, humectants to prevent toothpaste from drying out, thickeners, and preservatives to prevent the growth of microorganisms, flavoring agents, sweeteners, and coloring agents.

At least some portion of a serving size of toothpaste is swallowed during brushing, even if not intended. The portion of the toothpaste which is swallowed, including any dietary ingredient(s) therein, is digested in the gastrointestinal tract. Known toothpastes which include vitamins and/or minerals, however, fail to provide the vitamins and/or minerals such as, B-complex of vitamins, Vitamin C, and calcium, for example, in an amount sufficient to be considered a "significant source" of the dietary supplement(s) included therein.

The term "dietary supplement" was defined in the Dietary Supplement Health and Education Act (DSHEA) of 1994. In short, a dietary supplement is a product taken orally that contains a dietary ingredient intended to supplement the diet. The dietary ingredients may include, for example, vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. The DSHEA places dietary supplements in a special category under the general umbrella of foods, not drugs. In particular, if a product contains less than 2 percent of the reference daily intake (RDI) of a given dietary supplement, that product is not a "significant source" of that dietary supplement.

Therefore, what is needed on the market today is a toothpaste that provides a significant source of at least one dietary supplement, such as a vitamin and/or a mineral and does not include fluoride. That is, a non-fluoride toothpaste containing more than 2 percent of the reference daily intake (RDI) of a given dietary supplement that is safe to swallow and supplements the diet of a mammal when ingested is needed on the market today. The present invention provides such toothpaste and is further described in the sections below.

SUMMARY OF THE INVENTION

The present invention provides a non-fluoride containing toothpaste that is a significant source of at least one dietary supplement, such as a vitamin and/or a mineral; and a method of use therefor. In particular, the non-fluoride containing toothpaste of the present invention is formulated so that it does not include fluoride and therefore is not considered to be a drug under classifications set by the Food and Drug Administration (FDA). Desirably, the non-fluoride containing toothpaste is safe to swallow. Most desirably, the non-fluoride containing toothpaste contains at least one dietary supplement that when ingested supplements the diet of a mammal.

In one embodiment, a non-fluoride containing toothpaste enriched with at least one dietary supplement comprises a gum base, a thickening agent, at least one dietary supplement selected from the group consisting of vitamin B1, vitamin B6, vitamin A, vitamin D3, vitamin E, niacinamide, vitamin B12, D-calcium pantothenate and mixtures thereof. In addition the non-fluoride toothpaste also comprises at least one component selected from the group consisting of sodium selanate, manganese chloride, zinc lactate, magnesium sulfate, sea salt, tetrasodium pyrophosphate and mixtures thereof. The non-fluoride containing toothpaste may further comprise a preservative and/or a flavoring agent.

In another embodiment of the present invention, a non-fluoride containing toothpaste enriched with at least one dietary supplement is provided comprising a gum base (A); a component (B) comprising at least one component selected from the group consisting of sodium saccharin, EDTA, sodium benzoate, stevia, xylitol, a polymer of ethylene oxide generally having the formula $H(OCH_2CH_2)_nOH$ wherein n has an average number of about 8 (PEG-8) and mixtures thereof; a component (C) comprising at least one component selected from the group consisting of: glycerin, propylparaben, titanium dioxide, sorbitol, and mixtures thereof; a component (D) comprising at least one component selected from the group consisting of: vitamin B1, vitamin B6, vitamin A, vitamin D3, vitamin E, niacinamide, vitamin B12, D-calcium pantothenate, and mixtures thereof; a component (E) comprising at least one component selected from the group consisting of: sodium selanate, manganese chloride, zinc lactate, magnesium sulfate, sea salt, tetrasodium pyrophosphate, and mixtures thereof; a component (F) comprising at least one component selected from the group consisting of: a precipitated amorphous silica having an average particle size of about 8.0 microns to about 11.0 microns known as Zeodent®113 available from J.M. Huber Corporation, Dicalcium phosphate dihydrate, a precipitated amorphous silica having an average particle size of about 11.0 microns to about 14.0 microns known as Zeodent® 165 available from J.M. Huber Corporation, and mixtures thereof; and a component (G) comprising at least one component selected from the group consisting of: natural spearmint oil, sodium lauryl sulfate, and mixtures thereof.

In one particular embodiment of the present invention, a non-fluoride containing toothpaste enriched with at least one dietary supplement is provided, as described above, further comprising pigmented and/or non-pigmented beads containing vitamins and/or minerals. As such, the toothpaste of the present invention contains vitamins and minerals as ingredients in the paste of the final toothpaste product, as well as beads which contain additional vitamins and/or minerals. By providing vitamins and/or minerals in beads in addition to the vitamins and minerals included as ingredients in the paste, an amount of vitamins and/or minerals may be provided that exceeds the amount of vitamins and/or minerals that can be included as ingredients in the final toothpaste product without precipitation from the toothpaste. Indeed, only a certain amount of dietary supplements, such as vitamins and/or minerals, may be incorporated as ingredients in the paste of the final toothpaste product without rendering the final toothpaste product insufficient as a toothpaste. For example, if the amount of vitamins and/or minerals incorporated as ingredients in the paste of the final toothpaste product exceeds a certain threshold, the vitamins and/or minerals may precipitate out of the paste, may become too runny or may have a foul taste and/or smell. Indeed, the degradation of certain vitamins and minerals has been found to cause discoloration because the degradation products produced by the exposure to air, for example, are a different color than the original compound. Therefore, the toothpaste of the present invention provides dietary supplements, such as vitamins and/or minerals, in beads, in addition to the vitamins and minerals included as ingredients in the paste of the final toothpaste product so as to provide a significant source of dietary supplement(s) when ingested.

Furthermore, providing dietary supplements, such as vitamins and/or minerals, in beads, as further discussed hereinbelow, can prevent such dietary supplements from being directly absorbed through the mucus membranes in the mouth, therefore allowing more of the dietary supplements to be digested in the gastrointestinal tract. Moreover, providing dietary supplements, such as vitamins and/or minerals, in beads can prevent such dietary supplements from being degraded in the acidic environment of the stomach, for example, thus allowing the vitamins and minerals to be absorbed in the gastrointestinal tract.

In one embodiment of the present invention, the beads containing the dietary supplement(s), such as vitamins and/or minerals, are comprised of a mixture of at least two components selected from the group consisting of: mannitol, cellulose, and hydroxypropyl methylcellulose. In another embodiment, the beads containing the dietary supplement(s) further comprises custom pigments and custom additives such as, herbs, botanicals, and flavorings.

The term "serving" or "serving size" shall be understood herein to mean an amount of food customarily consumed per eating occasion by persons 4 years of age or older which is expressed in a common household measure that is appropriate to the food. When the food is specially formulated or processed for use by infants or by toddlers, a "serving" or "serving size" means an amount of food customarily consumed per eating occasion by infants up to 12 months of age or by children 1 through 3 years of age, respectively. For example, a serving size of the present invention is equivalent to about a 1-inch strip on a standard toothbrush, which is about 1.0 g to 2.5 g of which at least a portion is ingested either directly or over a short period of time as residue that remains in the mouth after brushing.

The term "dietary ingredient" shall be understood herein to include vitamins, minerals, herbs or other botanicals, amino acids, and substances such as enzymes, and metabolites.

The term "dietary supplement" shall be understood herein to include any product taken by mouth that contains a "dietary ingredient," as defined above, which is intended to supplement the diet by ingestion. Dietary supplements can be extracts or concentrates, and may be found in many forms such as beads, pastes, tablets, capsules, softgels, gelcaps, liquids, or powders.

The term "reference daily intake" (RDI) shall be understood herein to refer to the estimated daily intake values for vitamins, minerals, and other dietary ingredients established by the FDA. For example, the RDI for vitamin B1 is about 1.1 mg; the RDI for vitamin B6 is about 2.0 mg; the RDI for vitamin A is about 5,000 International Units (IU); the RDI for vitamin D3 is about 400 IU; the RDI for vitamin E is about 30 IU; the RDI for niacinamide is about 18 mg; the RDI for vitamin B12 is about 6 micrograms (µg); the RDI for D-calcium pantothenate is about 10.0 mg; the RDI for sodium selanate is about 70 µg; the RDI for zinc lactate is about 15 mg; the RDI for magnesium sulfate is about 400 mg; and the RDI for sea salt is about 2300 mg.

The expression "significant source," when referring to a product including at least one dietary supplement, shall be understood to mean that the product includes at least 2% of the RDI for the dietary supplement(s) included therein.

The term "beads" shall be understood herein to include any substances that are capable of entrapping a material within the substance to form a barrier between the outside medium and the entrapped material.

The term "toothpaste" shall be understood herein to mean a non-fluoride containing composition.

The term PEG-8 is a polymer of ethylene oxide generally having the formula $H(OCH_2CH_2)_nOH$ wherein n has an average number of about 8 as defined in *CTFA International Cosmetic Ingredient Dictionary*, $4^{th}$ edition, published by The Cosmetic, Toiletry, and Fragrance Association Washington, D.C.

Zeodent®113 is a precipitated amorphous silica having an average particle size of about 8.0 microns to about 11.0 microns known as Zeodent®113 available from J.M. Huber Corporation used as a thickening agent and/or a dental abrasive.

Zeodent®165 is a precipitated amorphous silica having an average particle size of about 11.0 microns to about 14.0 microns known as Zeodent®113 available from J.M. Huber Corporation used as a thickening agent and/or a dental abrasive.

EDTA is a widely used acronym for the chemical compound ethylene diamine tetra acetic acid. EDTA is a polyamino carboxylic acid with the formula $[CH_2N(CH_2CO_2H)_2]_2$. This colorless, water-soluble solid produced on a large scale for many applications. Its prominence as a chelating agent arises from its ability to "sequester" di- and tricationic metal ions such as $Ca^{2+}$ and $Fe^{3+}$. After being bound by EDTA, metal ions remain in solution but exhibit diminished reactivity.

The above-disclosed embodiments of the present invention are further described in greater detail in the Detailed Description of the Invention directly following.

DETAILED DESCRIPTION OF THE INVENTION

The present invention may be understood more readily by reference to the following detailed description of the present invention, which forms a part of this disclosure. It is to be understood that the present invention is not limited to the specific devices, methods, conditions or parameters described and/or shown herein, and that the terminology used herein is for the purpose of describing particular embodiments by way of example only and is not intended to be limiting of the claimed invention.

The carriers or excipients of the present invention may be chosen to provide an appropriate mode of delivery, for example, solutions, colloidal dispersions, emulsions, suspensions, gels, powders, solids, and the like, and can include conventional components typically associated with toothpastes, and the like. Carriers suitable for the preparation of components of the present invention are well known in the art. Their selection will depend on secondary considerations like taste, cost, shelf stability and the like.

In one embodiment of the present invention, a non-fluoride containing toothpaste enriched with at least one dietary supplement comprising a gum base, a thickening agent, at least one component selected from the group consisting of: vitamin B1, vitamin B6, vitamin A, vitamin D3, vitamin E, niacinamide, vitamin B12, D-calcium pantothenate, and mixtures thereof, and at least one component selected from the group consisting of: sodium selanate, manganese chloride, zinc lactate, magnesium sulfate, sea salt, tetrasodium pyrophosphate, and mixtures thereof. The non-fluoride containing toothpaste may further comprise a preservative and/or a flavoring agent. In a preferred embodiment, the toothpaste of the present invention has a white shiny appearance.

In another embodiment of the present invention, a non-fluoride containing toothpaste enriched with at least one dietary supplement is provided comprising a gum base (A); a component (B) comprising at least one component selected from the group consisting of: sodium saccharin, EDTA, sodium benzoate, stevia, xylitol, PEG-8 and mixtures thereof; a component (C) comprising at least one component selected from the group consisting of: glycerin, propylparaben, titanium dioxide, sorbitol and mixtures thereof; a component (D) comprising at least one component selected from the group consisting of: vitamin B1, vitamin B6, vitamin A, vitamin D3, vitamin E, niacinamide, vitamin B12, D-calcium pantothenate and mixtures thereof; a component (E) comprising at least one component selected from the group consisting of: sodium selanate, manganese chloride, zinc lactate, magnesium sulfate, sea salt, tetrasodium pyrophosphate and mixtures thereof; a component (F) comprising at least one component selected from the group consisting of: Zeodent®113, Dicalcium phosphate dihydrate, Zeodent®165 and mixtures thereof; and a component (G) comprising at least one component selected from the group consisting of: natural spearmint oil, sodium lauryl sulfate and mixtures thereof.

Gum base (A) is included to thicken the final toothpaste product so as to result in a paste, rather than a liquid. Gum base (A) may include any gum base known in the art suitable for toothpastes including, for example, chicle, xanthan gum, guar gum, or a polybutene. In one embodiment of the present invention, gum base (A) is a cellulose gum such as carboxymethylcellulose and/or xanthan gum, or the like. Gum base (A) may be prepared by dissolving carboxymethylcellulose in hot water, adding xanthan gum, and mixing well. However, it is envisioned that gum base (A) may be produced according to any method known in the art for producing gum bases suitable for use in toothpastes.

In yet another embodiment of the present invention, Component (B) comprises at least one component selected from the group consisting of: sodium saccharin, EDTA, sodium benzoate, stevia, xylitol, PEG-8, and mixtures thereof. Sodium saccharin, stevia, and xylitol are provided as sweeteners, to improve the taste of the final toothpaste product. Xylitol is provided to reduce tooth decay by significantly decreasing plaque accumulation. EDTA is provided as a chelating agent to remove traces of metal ions which might otherwise cause dietary ingredients to deteriorate and clinically to reduce absorption of a mineral, or to increase its excretion. PEG-8 is provided as a thickener to prevent bacteria from breaking down pyrophosphates used to control tartar buildup.

In still yet another embodiment of the present invention, the toothpaste of the present invention includes a sweetener known in the art to sweeten toothpastes, such as cyclamate, aspartame, sorbitol, and maltitol, for example, in the place of sodium saccharin and/or stevia and/or xylitol, or the like. It is envisioned that the choice of sweetener may depend upon, for example, the desire to use natural or artificial sweetener, the amount of sweetening desired, and the other ingredients in the toothpaste. A chelating agent, such as a citrate, tartrate, or phosphate, for example, known in the art which is suitable for use in toothpastes is included in the place of EDTA. It is envisioned that the chelating agent used will be selected depending upon, for example, the amount of metal ions present. A thickener, such as polyethylene glycol of various weights and silicate, for example, known in the art which is suitable for thickening toothpaste is included in place of PEG-8, or the like. It is envisioned that the thickener used will be selected depending upon, for example, the desired consistency of the final toothpaste product.

In another embodiment of the present invention, described above, toothpaste comprises at least one component selected from the group consisting of: glycerin, propylparaben, titanium dioxide, sorbitol, and mixtures thereof. Glycerin and sorbitol are humectants which are provided to prevent the final toothpaste product from drying out. Propylparaben is provided as a preservative. Titanium dioxide is a whitener provided to whiten teeth.

In yet another embodiment of the present invention, the toothpaste includes a humectant, such as propylene glycol, xylitol, water, for example, known in the art which is suitable for use in toothpastes, in the place of glycerin and/or sorbitol, or the like. It is envisioned that the humectant used will be selected depending upon, for example, the susceptibility of the final toothpaste product to drying. A preservative, such as sodium benzoate, methyl paraben, and ethyl paraben, for example, that is known in the art to be suitable for use in toothpastes, can be included in place of propylparaben. It is envisioned that the preservative used will be selected depending upon, for example, the ingredients in the final toothpaste product. A whitener, such as peroxide, for example, known in the art that is suitable for use in toothpastes may be included in place of titanium dioxide. It is envisioned that the whitener used will be selected depending upon, for example, the desired whitening effect.

The non-fluoride containing toothpaste enriched with at least one dietary supplement includes vitamins, minerals and additives that have specific effects on the user. For example, vitamins A, D, and E promote healthy teeth and bones; vitamin B-complexes maintain healthy skin and gums; zinc supports the immune system; minerals strengthen bones and teeth; silica whitens teeth; and xylitol prevents plaque.

In still yet another embodiment of the present invention, the toothpaste comprises at least one component selected from the group consisting of: Zeodent®113, Dicalcium phosphate dihydrate, Zeodent®165, and mixtures thereof. Zeodent®113 is provided as an abrasive/polishing agent which helps to clean and whiten teeth. Dicalcium phosphate dihydrate is provided as a dental polishing product to help whiten teeth. Zeodent®165 is provided both as an abrasive/polishing agent and as a thickener.

In another embodiment of the present invention described above, the toothpaste may comprise natural spearmint oil, sodium lauryl sulfate, and mixtures thereof. Spearmint oil is provided to enhance the flavor of the final toothpaste product. Sodium lauryl sulfate is provided as a detergent/foaming agent.

In yet another embodiment of the present invention, the toothpaste comprises an agent known in the art that is suitable for use in toothpastes to enhance the flavor of the final toothpaste product, such as anise, peppermint, wintergreen, clove or cinnamon oil, for example, in place of natural spearmint oil. It is envisioned that the flavoring agent used will be selected depending upon, for example, the desired flavor of the final toothpaste product and the ingredients used. A detergent/foaming agent known in the art, which is suitable for use in toothpastes is provided in place of sodium lauryl sulfate.

All weight percent formulations provided in this disclosure are based on the total weight of the toothpaste.

In still yet another embodiment of the present invention, a non-fluoride containing toothpaste enriched with at least one dietary supplement is provided wherein the toothpaste comprises about 0.1 to about 1.0 percent by weight of gum base; about 0.20 to about 0.40 percent by weight sodium saccharin; about 0.05 to about 1.5 percent by weight ethylene diamine tetraacetic acid (EDTA); about 0.20 to about 0.40 percent by weight sodium benzoate; about 0.3 to about 0.4 percent by weight stevia; about 5.0 to about 7.0 percent by weight xylitol; about 0.02 to about 0.06 percent by weight of a polymer of ethylene oxide generally having the formula $H(OCH_2CH_2)_n OH$ wherein n has an average number of about 8; about 26.0 to about 28.0 percent by weight glycerin; about 0.05 to about 0.15 percent by weight propylparaben; about 0.4 to about 0.6 percent by weight titanium dioxide; about 12.0 to about 14.0 percent by weight sorbitol; about $2.5 \times 10^{-5}$ to about $2.5 \times 10^{-3}$ percent by weight vitamin B1; about $2.5 \times 10^{-5}$ to about $2.5 \times 10^{-3}$ percent by weight vitamin B6; about $2.5 \times 10^{-5}$ to about $2.5 \times 10^{-3}$ percent by weight vitamin A; about $2.5 \times 10^{-4}$ to about $5.0 \times 10^{-4}$ percent by weight vitamin D3; about $5.0 \times 10^{-4}$ to about $2.0 \times 10^{-3}$ percent by weight vitamin E; about 0.07 to about 1.0 percent by weight niacinamide; about $2.5 \times 10^{-5}$ to about $4 \times 10^{5}$ percent by weight vitamin B12; about 0.03 to about 0.06 percent by weight D-calcium pantothenate; about $6.0 \times 10^{-4}$ to about $9.0 \times 10^{-4}$ percent by weight sodium selanate; about 0.025 to about 0.04 percent by weight manganese chloride; about 0.2 to about 0.40 percent by weight zinc lactate; about 0.6 to about 0.9 percent by weight magnesium sulfate; about 0.05 to about 0.15 percent by weight sea salt; about 0.6 to about 0.8 percent tetrasodium pyrophosphate; about 4.0 to about 6.0 percent by weight of a precipitated amorphous silica having an average particle size of about 8.0 microns to about 11.0 microns; about 1.5 to about 2.0 percent by weight dicalcium phosphate dihydrate; about 8.0 to about 10 percent by weight of a precipitated amorphous silica having an average particle size of about 8.0 microns to about 11.0 microns for abrasive and/or thickening; about 0.5 to about 1.5 percent by weight spearmint oil and about 1.0 to about 1.5 percent by weight sodium lauryl sulfate; and water.

The non-fluoride enriched toothpaste of the present invention may further comprises about 3.0 to about 4.0 percent by weight of polyethylene glycol (PEG-8), about 0.4 to about 0.6 percent by weight of pigmented beads, about 0.2 to about 0.35 percent by weight of rentinyl palmitate and cholecalciferol. The pigmented beads may be made from a mixture of mannitol, cellulose, hydroxypropyl methylcellulose, and may comprise at least one dietary supplement.

The toothpaste of the present invention may be formulated by first dissolving component (B) in component (A) in a container to form AB. It is envisioned that component (B) may be admixed with component (A) to form an admixture of AB. Propylparaben is dissolved in the glycerin from component (C) in another container. Next, titanium dioxide is added and mixed. The mixture including propylparaben, glycerin, titanium dioxide, and other components of component (C), save sorbitol, is then transferred to the container containing AB. A portion of the sorbitol solution from component (C) is used to rinse titanium dioxide and/or glycerin from the container, and is transferred to the container containing AB. The remaining sorbitol solution is then added to form ABC. It is envisioned that the components of ABC may be admixed to form an admixture of ABC. Next, component (D) is added to ABC, dissolved, and mixed to form ABCD. It is envisioned that each ingredient from component (D) may be added separately and mixed following the addition of each ingredient. It is also envisioned that component (D) may be admixed with ABC to form an admixture of ABCD. Component (E) is added to ABCD and mixed to form ABCDE. It is envisioned that each ingredient from component (E) may be added separately and mixed following the addition of each ingredient. It is also envisioned that component (E) may be admixed with ABCD to form an admixture of ABCDE. Next, component (F) is added to ABCDE to form ABCDEF. The spearmint oil from component (G) is then added to ABCDEF and mixed. Lastly, sodium lauryl sulfate is added to the mixture of ABCDEF and spearmint oil and mixed to form ABCDEFG. ABCDEFG should be mixed gently following the addition of sodium lauryl sulfate to avoid foaming. However, it is envisioned that the non-fluoride containing toothpaste of the present invention may be produced by any method known in the art for producing toothpaste.

The final toothpaste product may be adjusted so as to have a neutral pH. In a preferred embodiment of the present invention, the pH of the final toothpaste product is about 6.0 to about 7.0, preferably 6.0 to about 6.5, and more preferably a pH of 6.1.

In one particular embodiment of the present invention, a non-fluoride containing toothpaste enriched with at least one dietary supplement is provided, as described above, further comprising beads containing at least one dietary supplement such as vitamins and/or minerals. Beads used in the present invention may be available from Induchem USA, Inc. located in New York. As such, the non-fluoride containing toothpaste of the present invention contains vitamins and minerals as ingredients in the paste of the final toothpaste product, as well as beads which contain additional vitamins and/or minerals. By providing vitamins and/or minerals in beads in addition to the vitamins and minerals included as ingredients in the paste, an amount of vitamins and/or minerals may be provided which exceeds the amount of vitamins and/or minerals which can be included as ingredients in the paste of the final toothpaste product alone. Indeed, only a certain amount of dietary supplements, such as vitamins and/or minerals, may be incorporated as ingredients in the paste of the final toothpaste product without rendering the final toothpaste product insufficient as a toothpaste. For example, if the amount of vitamins and/or minerals incorporated as ingredients in the paste of the final toothpaste product exceeds a certain threshold, the paste may become too runny or may have a foul taste and/or smell.

Indeed, the degradation of certain vitamins and minerals has been found to cause discoloration of the toothpaste because the degradation products produced by the exposure to air, for example, are a different color than the original compound. Therefore, the toothpaste of the present invention provides dietary supplements, such as vitamins and/or minerals, in beads, in addition to the vitamins and minerals included as ingredients in the paste of the final toothpaste product, in an amount such that the final toothpaste product is a significant source or the dietary supplement(s) included therein.

Furthermore, it is envisioned that providing dietary supplements, such as vitamins and/or minerals, in beads can prevent such dietary supplements from being directly absorbed through the mucus membranes in the mouth, therefore allowing the dietary supplements to be digested in the gastrointestinal tract. Moreover, it is envisioned that providing dietary supplements, such as vitamins and/or minerals, in beads can prevent such dietary supplements from being degraded in the acidic environment of the stomach, for example, thus allowing the vitamins and minerals to be absorbed in the gastrointestinal tract.

The beads containing at least one dietary supplement also create friction during brushing, which enhances the ability of the toothpaste to clean and maintain the aesthetics and health of teeth, thus providing better oral hygiene.

In one embodiment of the present invention, the beads containing the dietary supplement(s), such as vitamins and/or minerals, are comprised of mannitol, cellulose, and hydroxypropyl methylcellulose. It is envisioned that the beads containing the dietary supplement (s) further comprise custom pigments and additives. In another embodiment of the present invention, the beads containing the dietary supplement (s) entrap the dietary ingredient(s), pigments, and actives within the mannitol, cellulose, and hydroxypropyl methylcellulose components of the beads. As such, a dried paste which includes a matrix of the dietary supplement (s), pigments, actives, mannitol, cellulose, and hydroxypropyl methylcellulose is produced, which, when swallowed, will release the dietary supplement (s) to be later absorbed in the body. In particular, by providing at least one dietary supplement entrapped within the mannitol, cellulose, and hydroxypropyl methylcellulose components of the beads, the dietary supplement (s) can be gradually released from the matrix, rather than released all at once, thus allowing the dietary supplement (s) to be absorbed in the body over time.

It should be recognized that the beads containing at least one dietary supplement of the present invention are distinguishable from beads heretofore used in toothpastes that include at least one dietary supplement, such as a vitamin or mineral, for example. Indeed, known toothpastes which include at least one dietary supplement encapsulate the dietary supplement (s) in cellulose without other alcohols or components which make the beads break instead of creating a film-like component, for example. These types of encapsulated dietary supplement (s) have a glass-like shell which break to release the contained dietary supplement(s) all at once. Indeed, because the encapsulated dietary supplement (s) is/are released when the glass-like shell is broken, these types of encapsulated dietary supplement (s) are incapable of releasing the dietary supplement (s) over time and less of the vitamins/minerals are likely to be ingested as a dietary supplement.

Non-fluoride containing toothpastes of the present invention, that include beads made from cellulose and other alcohols or components, and contain at least one dietary supplement such as vitamins and/or minerals, may be produced by first dissolving component (B) in component (A) in a container to form AB. Propylparaben is dissolved in the glycerin from component (C) in another container. Next, titanium dioxide is added and mixed. The mixture including propylparaben, glycerin, titanium dioxide, and any other components of component (C), save sorbitol, is then transferred to the container containing AB. A portion of the sorbitol solution from component (C) is used to rinse titanium dioxide and/or glycerin from the container, and is transferred to the container containing AB. The remaining sorbitol solution is then added to form ABC. Next, component (D) is added to ABC, dissolved, and mixed to form ABCD. Component (E) is added to ABCD and mixed to form ABCDE. Next, component (F) is added to ABCDE to form ABCDEF. The spearmint oil from component (G) is then added to ABCDEF and mixed. Next, the beads containing at least one dietary supplement are added to the mixture of ABCDEF and spearmint oil, and mixed gently. Lastly, sodium lauryl sulfate is added and mixed to form ABCDEFG. ABCDEFG should be mixed gently following the addition of the beads containing at least one dietary supplement and/or sodium lauryl sulfate to avoid breaking the beads and/or foaming.

In yet another embodiment, a method for delivering at least one dietary supplement to a mammal is provided in which a dose of the toothpaste of the present invention, about 1 to about 2 grams, is applied to the teeth of a mammal either on a toothbrush or directly. The applied toothpaste is then used to clean and/or polish the teeth of the mammal. In doing so, at least a portion of the toothpaste, which contains at least one dietary supplement, is ingested by the mammal and supplements the diet of the mammal. This method can be repeated multiple times in a 24-hour period and preferably is repeated at least three times in a 24-hour period.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A non-fluoride containing dietary supplement enriched toothpaste suitable for ingestion, said toothpaste comprising:
   (a) a dentally acceptable oral vehicle containing sufficient amount of a thickening agent to impart a pasty consistency; and
   (b) a dietary supplement,
   wherein said dietary supplement is provided in beads which i) prevent the dietary supplement from being absorbed through the mucus membranes in the mouth, and ii) prevent the dietary supplements from being degraded in the acidic environment of the stomach, and wherein a serving size amount of said toothpaste contains more than about 2 percent of the reference daily intake (RDI) of said dietary supplement and wherein said toothpaste is formulated so that multiple ingestions of at least a portion of said serving size amount provide at least 2 percent of the RDI of the dietary supplement.

2. The toothpaste of claim 1 wherein the dietary supplement comprises one or more of vitamin B1, Vitamin A, vitamin B-12, vitamin B6, vitamin D3, vitamin E, niacinamide, D-calcium pantothenate, sodium selenate, manganese chloride, and zinc lactate.

3. The toothpaste of claim 1 wherein the dietary supplement comprises a mixture of vitamin B6, vitamin D3, vitamin E, niacinamide, D-calcium pantothenate, sodium selenate, manganese chloride and zinc lactate.

4. The toothpaste of claim 1 wherein the dentally acceptable oral vehicle comprises a preservative.

5. The toothpaste of claim 4, wherein the preservative is selected from the group consisting of ethylene diamine tetraacetic acid (EDTA), propylparaben and mixtures thereof.

6. The toothpaste of claim 1 wherein the dentally acceptable oral vehicle comprises a flavoring agent.

7. The toothpaste of claim 6 wherein said flavoring agent is selected from the group consisting of sodium saccharin, stevia, natural spearmint oil and mixtures thereof.

8. The toothpaste of claim 1 wherein the dentally acceptable oral vehicle comprises at least one component selected from the group consisting of a cleaning and/or polishing agent, non-fluoride anti-cavity agent, toothpaste whitening agent, moisture retaining agent, foaming agent, pigment and abrasive.

9. The toothpaste of claim 8 wherein said non-fluoride anti cavity agent is xylitol, said toothpaste whitening agent is titanium dioxide, said moisture retaining agent is glycerin and/or sorbitol, said foaming agent includes sodium lauryl sulfate, and said abrasive is a polymer of ethylene oxide generally having the formula $H(OCH_2CH_2)_nOH$ wherein n has an average number of about 8 and/or precipitated amorphous silica having an average particle size of about 8.0 to about 14.0 microns.

10. The toothpaste of claim 1, further comprising a plurality of pigmented beads dispersed throughout said toothpaste.

11. The toothpaste of claim 10, wherein the pigmented beads contain at least one dietary supplement.

12. The toothpaste of claim 11, wherein the beads are comprised of mannitol, cellulose and hydroxypropyl methylcellulose.

13. A non-fluoride containing dietary supplement enriched toothpaste suitable for ingestion, said toothpaste comprising:
   a gum base as component (A);
   a mixture of sodium saccharin, ethylene diamine tetraacetic acid (EDTA), sodium benzoate, stevia, xylitol, a polymer of ethylene oxide having the general formula $H(OCH_2CH_2)_nOH$ wherein n has an average number of about 8 as component (B);
   a mixture of glycerin, propylparaben, titanium dioxide, sorbitol as component (C);
   a mixture of vitamin B6, vitamin D3, vitamin E, niacinamide, D-calcium pantothenate as component (D);
   a mixture of sodium selenate, manganese chloride, zinc lactate, magnesium sulfate, sea salt, tetrasodium pyrophosphate as component (E);
   precipitated amorphous silica having an average particle size of about 8.0 to about 14 microns for both abrasive and/or thickening and dicalcium phosphate dihydrate as component (F);
   at least one flavoring agent as component (G); and
   water,
   wherein the combination of components ABCDEFG is formed by the sequential addition of component B to component A to form the combination AB, the addition of component C to AB to form the combination ABC, the addition of component D to ABC to form the combination ABCD, the addition of component E to ABCD to form the combination ABCDE, the addition of component F to ABCDE to form the combination ABCDEF, and the combination of component G to ABCDEF to form the combination ABCDEFG
   wherein a serving size amount of said toothpaste contains more than about 2 percent of a reference daily intake (RDI) of dietary supplement, said dietary supplement comprising vitamin B6, vitamin D3, vitamin E, niacinamide, D-calcium pantothenate sodium selenate, manganese chloride, and zinc lactate, and wherein said toothpaste is formulated so that multiple ingestions of at least a portion of said serving size amount provide at least 2 percent of the RDI of the dietary supplement.

14. The toothpaste of claim 13 wherein component (G) is selected from the group consisting of natural spearmint oil, sodium lauryl sulfate, and mixtures thereof.

15. The toothpaste of claim 13 wherein the toothpaste further comprises about 3.0 to about 4.0 percent by weight of polyethylene glycol (PEG-8), about 0.4 to about 0.6 percent by weight of pigmented beads, about 0.2 to about 0.35 percent by weight of rentinyl palmitate and cholecalciferol.

16. The toothpaste of claim 13 further containing a plurality of pigmented beads dispersed throughout said toothpaste.

17. The toothpaste of claim 15, wherein the beads are comprised of mannitol, cellulose, hydroxypropyl methylcellulose, and at least one of vitamin B6, vitamin D3, vitamin E, niacinamide, D-calcium pantothenate sodium selenate, manganese chloride, and zinc lactate.

18. A method for delivering at least one dietary supplement to a mammal comprising:
   (a) brushing the teeth of a mammal with the toothpaste of claim 1; and
   (b) ingesting at least a portion of said toothpaste thereby supplementing the diet of said mammal.

19. The method of claim 18, wherein said steps (a) and (b) are repeated at least three times in a 24 hour period.

20. A method for delivering at least one dietary supplement to a mammal comprising:
   (a) brushing the teeth of a mammal with the toothpaste of claim 13; and
   (b) ingesting at least a portion of said toothpaste thereby supplementing the diet of said mammal.

* * * * *